United States Patent [19]

Lantzsch

[11] Patent Number: 4,472,577
[45] Date of Patent: Sep. 18, 1984

[54] PREPARATION OF α-HYDROXY-PHOSPHONIC ACID ESTERS

[75] Inventor: Reinhard Lantzsch, Leverkusen, Fed. Rep. of Germany

[73] Assignee: Bayer Aktiengesellschaft, Leverkusen, Fed. Rep. of Germany

[21] Appl. No.: 398,725

[22] Filed: Jul. 15, 1982

[30] Foreign Application Priority Data

Jul. 31, 1981 [DE] Fed. Rep. of Germany ....... 3130433

[51] Int. Cl.$^3$ .................. C07F 9/40; C07C 45/00
[52] U.S. Cl. ...................... 544/243; 546/22; 546/314; 544/335; 260/937; 260/953; 568/426; 568/420; 568/449; 568/485; 568/488
[58] Field of Search ............ 544/243; 546/22; 260/953, 968, 937

[56] References Cited

U.S. PATENT DOCUMENTS 4,317,783  3/1982  Hoffman .................. 260/937

FOREIGN PATENT DOCUMENTS 0024611  3/1981  Fed. Rep. of Germany ...... 568/426

OTHER PUBLICATIONS

Noller, Chemistry of Organic Compounds, W. B. Saunders Co., Philadelphia, (1965), p. 236.
Horner, et al., Chem. Ber., 103, No. 9, pp. 2984–2986, (1970).
Israel Journal of Chemistry, vol. 9, 1971, pp. 35–44, Reactions of Dimethyl Benzoylphosphonate, I. Shahak & J. Peretz.
Israel Journal of Chemistry, vol. 4, 1966, pp. 225–231, The Reaction of α-Ketophosphonates with Organometallic Compounds and Sodium Borohydride, I. Shahak and E. D. Bergmann.

Primary Examiner—Donald G. Daus
Assistant Examiner—Diana G. Rivers
Attorney, Agent, or Firm—Sprung, Horn, Kramer & Woods

[57] ABSTRACT

A process for the production of an α-hydroxy-phosphonic acid ester of the general formula

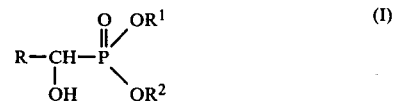

in which
R represents an optionally substituted aryl or heteroaryl group, and
$R^1$ and $R^2$ independently of each other represent an alkyl or phenyl group, or together represent an alkanediyl (alkylene) radical, comprising reacting α-oxo-phosphonic acid esters with hydrogen in the presence of a hydrogenation catalyst. The α-hydroxy-phosphonic acid esters of formula (I) are intermediate products for the production of pesticides.

5 Claims, No Drawings

PREPARATION OF α-HYDROXY-PHOSPHONIC ACID ESTERS

The present invention relates to an unobvious process for the production of known α-hydroxy-phosphonic acid esters.

It has already been disclosed that α-hydroxy-phosphonic acid esters are obtained when α-oxo-phosphonic acid esters are reacted with metals, such as zinc, in the presence of mercury (II) chloride, alloys, such as sodium amalgam, or hydride complexes, such as sodium boranate (see Israel J. Chem. 4 (1966), 225; ibid 9 (1971), 33; Chem. Ber. 103 (1970), 2984; and Houben-Weyl, Methoden der organischen Chemie (Methods of Organic Chemistry), 4th edition, Volume 12/1, page 512, Thieme-Verlag, Stuttgart 1963). For reasons of cost, the methods mentioned are not very suitable for use industrially.

According to the present invention we provide a process for the production of an α-hydroxy-phosphonic acid ester of the general formula

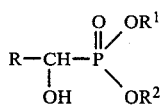  (I)

in which
R represents an optionally substituted aryl or heteroaryl group, and
$R^1$ and $R^2$ independently of each other represent an alkyl or phenyl group, or together represent an alkanediyl (alkylene) radical,
in which an α-oxo-phosphonic acid ester of the general formula

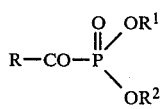  (II)

in which
R, $R^1$ and $R^2$ have the meanings given above, is reacted with hydrogen in the presence of a hydrogenation catalyst and in the presence of an inert diluent at a temperature between 20° and 200° C.

It is surprising that the reaction of α-oxo-phosphonic acid esters with hydrogen by the process according to the present invention leads to α-hydroxy-phosphonic acid esters in virtually quantitative yields, since, according to the literature (see Chem. Ber. 103, (1970), 2984), this reaction is supposed to give a small yield or no yield, and since it is furthermore known that complex substance mixtures are formed from oxo-phosphonic acid esters and nickel compounds (see Gazz. Chim. Ital. 107 (1977), 217).

The process according to the invention possesses various advantages compared with the stage of the art. The catalytic hydrogenation is cheaper than the reaction with the previously used reducing agents. By carrying out the reaction in a neutral medium, it is also possible to prepare compounds which contain base-sensitive groups.

If dimethyl benzoylphosphonate and hydrogen are used as the starting materials, in the presence of Raney nickel, the course of the process according to the invention is illustrated by the following equation:

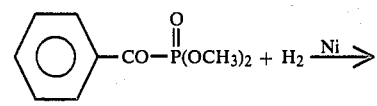

Preferred phosphonic acid esters of formula (II) to be used as starting materials in the process according to the invention are those in which,
R represents a pyridyl, pyrimidinyl or phenyl group which is optionally substituted by fluorine, chlorine, bromine, $C_1$ to $C_4$ alkyl, trifluoromethyl, trifluoromethoxy, $C_1$ to $C_4$ alkoxy and/or phenoxy,
$R^1$ represents a $C_1$ to $C_4$ alkyl or phenyl group, and
$R^2$ represents a $C_1$ $C_4$ alkyl or phenyl group, or
$R^2$ together with $R^1$ represents a straight-chain or branched $C_2$ to $C_5$ alkanediyl radical.

Starting compounds of the formula (II) are known and can be prepared from the appropriate carboxylic acid chlorides and phosphorous acid esters, according to processes which are in themselves known (see Houben-Weyl, Methoden der organischen Chemie (Methods of Organic Chemistry), 4th edition, Volume 12/1, pages 453–458, Thieme-Verlag, Stuttgart 1963; J.Am.Chem.-Soc. 86, (1964), 3862–3866; J.Org.Chem. 30 (1965), 1265–1268; ibid. 36 (1971), 128–136; DE-OS (German Published Specification) No. 2,917,620 and DE-OS (German Published Specification) No. 2,934,034).

The following may be mentioned as examples of the starting compounds of the formula (II): dimethyl and diethyl benzoylphosphonate, 3-methyl-benzoyl-phosphonate, 4-methyl-benzoyl-phosphonate, 3,4-dimethyl-benzoyl-phosphonate, 4-fluoro-benzoyl-phosphonate, 3-chloro-benzoyl-phosphonate, 4-chloro-benzoyl-phosphonate, 3,4-dichloro-benzoyl-phosphonate, 4-bromo-benzoyl-phosphonate, 3-bromo-4-fluoro-benzoyl-phosphonate, 4-tert.-butyl-benzoyl-phosphonate, 4-methoxy-benzoyl-phosphonate, 3,4-dimethoxy-benzoyl-phosphonate, 3-trifluoromethyl-benzoyl-phosphonate, 3-phenoxy-benzoyl-phosphonate and 4-fluoro-3-phenoxy-benzoyl-phosphonate.

The process according to the invention is carried out in the presence of a diluent. Preferred diluents are inert organic solvents. These include, as preferences, optionally halogenated hydrocarbons (such as hexane, heptane, cyclohexane, petroleum ether, petrol, ligroin, benzene, toluene, xylene, chlorobenzene, dichlorobenzene and decalin) and ethers (such as, for example, dibutyl ether, glycol dimethyl ether, diglycol dimethyl ether, tetrahydrofuran and dioxane).

The process according to the invention is carried out in the presence of a hydrogenation catalyst. Anhydrous, neutral metal catalysts (such as Raney nickel, Raney cobalt or palladium), optionally on customary carrier materials (such as charcoal), are preferably employed. Raney nickel is particularly preferred as the catalyst.

In carrying out the process according to the invention, the reaction temperatures can be varied within the stated relatively wide range of 20° and 200° C., and is preferably carried out at between 50° and 160° C., in particular at between 90° and 130° C.

The process according to the invention is carried out in general under elevated pressure, preferably between 5 and 200 bar, in particular between 10 and 100 bar.

To carry out the process according to the invention, generally between 1 and 100 g, preferably between 5 and 50 g, of catalyst are employed per mol of α-oxo-phosphonic acid ester of the formula (II).

The process according to the present invention is generally carried out as follows:

The starting material of the formula (II), the catalyst and the diluent are mixed, and hydrogen is forced in while the mixture is heated to the required temperature. Hydrogen is forced in at a constant temperature until the pressure remains constant, indicating the end of the reaction.

To isolate the product, the mixture is filtered and the solvent is distilled off carefully under reduced pressure.

The compounds to be prepared according to the invention can be used as intermediate products for the preparation of pest-combating agents (see U.S. application Ser. No. 307,256, filed Sept. 30, 1981, now pending).

PREPARATIVE EXAMPLES

Example 1

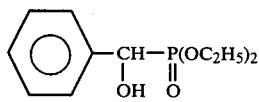

31.5 g (0.13 mol) of diethyl benzoyl-phosphonate were dissolved in 200 ml of tetrahydrofuran and 3 g of Raney nickel, which had been washed first with water, then with ethanol and then with tetrahydrofuran, were added to the solution. The mixture was heated to 120° C. under a hydrogen pressure of 40 bar and then hydrogenated with hydrogen at 80 to 90 bar. After the mixture had been worked up in a customary manner, 29.7 g of an oil was obtained which solidified after some time to give a crystalline mass consisting of pure diethyl α-hydroxy-benzyl-phosphonate. Yield: 93.5% of theory.

Example 2

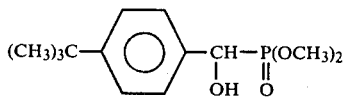

47.5 g (0.175 mol) of dimethyl 4-tert.-butyl-benzoyl-phosphonate were dissolved in 250 ml of tetrahydrofuran and 5 g of Raney nickel, which had been washed first with water, then with ethanol and then with tetrahydrofuran, were added to the solution. The mixture was heated to 135° C. under a hydrogen pressure of 55 bar and hydrogenated with hydrogen at 65 to 90 bar. The hydrogenation was complete after 40 minutes. After the catalyst had been filtered off and the tetrahydrofuran had been distilled off, 47.6 g of an oil were obtained which crystallized after a short time, after the last residues of tetrahydrofuran had been removed in a high vacuum. The dimethyl α-hydroxy-4-tert.-butyl-benzyl-phosphonate melted at 102° C. Yield: 100% of theory.

Example 3

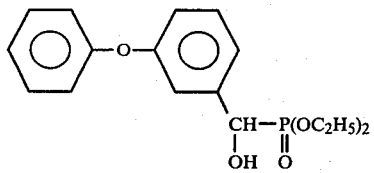

58.8 g (0.2 mol) of diethyl 3-phenoxy-benzoyl-phosphonate were dissolved in 300 ml of toluene and 10 g of Raney nickel, which had been washed first with water, then with ethanol and then with tetrahydrofuran, were added to the solution. The mixture was heated to 130° C. under a hydrogen pressure of 50 bar and hydrogenated with hydrogen at 80 to 90 bar. After the catalyst had been filtered off and the toluene had been distilled off, 59.1 g of a viscous oil remained which, according to the IR spectrum and NMR spectrum, was diethyl 3-phenoxy-α-hydroxy-benzyl-phosphonate.

Diethyl 3-phenoxy-4-fluoro-α-hydroxy-benzyl-phosphonate was also obtained analogously to the above example:

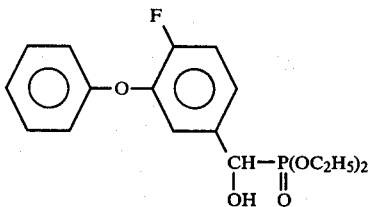

Example 4

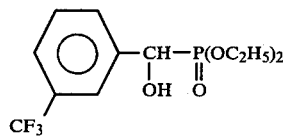

49.6 g (0.16 mol) of diethyl 3-trifluoromethyl-benzoyl-phosphonate were dissolved in 200 ml of tetrahydrofuran and 5 g of Raney nickel, which had been washed first with water, then with ethanol and then with tetrahydrofuran, were added to the solution. The mixture was hydrogenated at 125° C. under a hydrogen pressure of 75 to 90 bar. After the mixture had been worked up in the customary manner, 48.1 g of an oil was obtained which consisted of diethyl α-hydroxy-benzyl-phosphonate, according to IR and $^1$H-NMR. Yield: 96.4% of theory.

It will be understood that the specification and examples are illustrative but not limitative of the present invention and that other embodiments within the spirit and scope of the invention will suggest themselves to those skilled in the art.

I claim:

1. In the production of α-hydroxy-phosphonic acid ester of the formula

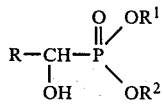

in which
R is an optionally substituted aryl or heteroaryl group, and
$R^1$ and $R^2$ each independently is an alkyl or phenyl group, or together are an alkanediyl radical,
by hydrogenating an α-oxo-phosphonic acid ester of the formula

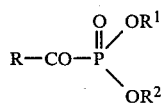

in the presence of an inert diluent at a temperature between about 20° and 200° C., the improvement which comprises effecting the hydrogenation in the presence of Raney nickel which has been washed to neutrality.

2. A process according to claim 1, in which
R is a pyridyl, pyrimidinyl or phenyl group which is optionally substituted by fluorine, chlorine, bromine, $C_1$ and $C_4$ alkyl, trifluoromethyl, trifluoromethoxy, $C_1$ to $C_4$ alkoxy and/or phenoxy,
$R^1$ and $R^2$ each independently is a $C_1$ to $C_4$ alkyl or phenyl group, or $R^2$ together with $R^1$ is a $C_2$ to $C_5$ alkanediyl radical.

3. A process according to claim 1, wherein the inert diluent is an inert organic solvent.

4. A process according to claim 1, wherein the reaction is carried out at a temperature between about 90° and 130° C.

5. A process according to claim 2, wherein the inert diluent is an inert organic solvent, and the reaction is carried out at a temperature between about 90° and 130° C.

* * * * *